United States Patent [19]

Roby et al.

[11] Patent Number: 5,522,841
[45] Date of Patent: Jun. 4, 1996

[54] ABSORBABLE BLOCK COPOLYMERS AND SURGICAL ARTICLES FABRICATED THEREFROM

[75] Inventors: Mark S. Roby, Killingworth; Cheng-Kung Liu, Norwalk; Steven L. Bennett, Southington, all of Conn.

[73] Assignee: United States Surgical Corporation, Norwalk, Conn.

[21] Appl. No.: 366,127

[22] Filed: Dec. 29, 1994

Related U.S. Application Data

[63] Continuation-in-part of Ser. No. 204,721, Mar. 2, 1994, Pat. No. 5,403,347, which is a continuation-in-part of Ser. No. 68,811, May 27, 1993, abandoned.

[51] Int. Cl.⁶ .......................... C08G 63/664; C08G 63/64; C08G 63/08

[52] U.S. Cl. .................. 606/230; 606/77; 606/151; 606/219; 525/408; 525/409; 525/411; 525/413; 525/415; 528/354

[58] Field of Search .................. 528/354; 525/408, 525/409, 411, 413, 415; 606/230, 77, 151, 219

[56] References Cited

U.S. PATENT DOCUMENTS

| | | | |
|---|---|---|---|
| 2,668,162 | 2/1954 | Lowe . | |
| 2,683,136 | 7/1954 | Higgins . | |
| 2,703,316 | 3/1955 | Schneider . | |
| 2,758,987 | 8/1956 | Salzberg . | |
| 3,225,766 | 12/1965 | Baptist et al. . | |
| 3,268,486 | 8/1966 | Klootwijk . | |
| 3,268,487 | 8/1966 | Klootwijk . | |
| 3,297,033 | 1/1967 | Schmitt . | |
| 3,422,181 | 1/1969 | Chirgwin, Jr. . | |
| 3,442,871 | 5/1969 | Schmitt et al. . | |
| 3,463,158 | 2/1969 | Schmitt et al. . | |
| 3,468,853 | 9/1969 | Schmitt et al. . | |
| 3,531,519 | 9/1970 | Trehu . | |
| 3,565,869 | 2/1971 | DeProspero . | |
| 3,597,449 | 8/1971 | DeProspero et al. . | |
| 3,620,218 | 11/1971 | Schmitt et al. . | |
| 3,626,948 | 12/1971 | Glick et al. . | |
| 3,636,956 | 1/1972 | Schneider . | |
| 3,733,919 | 5/1973 | Rupp, II | 74/242.6 |
| 3,736,646 | 6/1973 | Schmitt et al. | 29/438 |
| 3,772,420 | 11/1973 | Glick et al. . | |
| 3,781,349 | 12/1973 | Ramsey et al. . | |
| 3,784,585 | 1/1974 | Schmitt et al. . | |
| 3,792,010 | 2/1974 | Wasserman et al. . | |
| 3,797,499 | 3/1974 | Schneider | 128/33.4 R |
| 3,839,297 | 10/1974 | Wasserman et al. | 128/335.5 |
| 3,846,382 | 11/1974 | Ramsey et al. . | |
| 3,867,190 | 2/1975 | Schmitt et al. . | |
| 3,878,284 | 4/1975 | Schmitt et al. | 264/184 |
| 3,902,497 | 9/1975 | Casey | 128/296 |
| 3,937,223 | 2/1976 | Roth | 128/325 |
| 3,982,543 | 9/1976 | Schmitt et al. | 128/335.5 |
| 3,987,937 | 10/1976 | Coucher | 222/193 |
| 4,033,938 | 7/1977 | August et al. . | |
| 4,045,418 | 8/1977 | Sinclair . | |
| 4,052,988 | 10/1977 | Dotti et al. | 128/335.5 |
| 4,057,537 | 11/1977 | Sinclair . | |
| 4,060,089 | 11/1977 | Noiles | 128/325 |
| 4,137,921 | 2/1979 | Okuzumi et al. | 128/335.5 |
| 4,157,437 | 6/1979 | Okuzumi et al. | 528/354 |
| 4,243,775 | 1/1981 | Rosensaft et al. | 525/415 |
| 4,246,904 | 1/1981 | Kaplan | 525/444 |
| 4,273,920 | 6/1981 | Nevin | 528/361 |
| 4,275,813 | 6/1981 | Noiles | 206/339 |
| 4,279,249 | 7/1981 | Vert et al. | 525/415 |
| 4,300,565 | 11/1981 | Rosensaft et al. | 328/354 |
| 4,429,080 | 1/1984 | Casey et al. | 525/415 |
| 4,438,253 | 3/1984 | Casey et al. | 528/86 |
| 4,452,973 | 6/1984 | Casey et al. | 528/354 |
| 4,526,938 | 7/1985 | Churchill et al. | 525/415 |
| 4,643,191 | 2/1984 | Bezwada et al. | 525/415 |
| 4,653,497 | 3/1987 | Bezwada et al. | 525/415 |
| 4,705,820 | 11/1987 | Wang et al. | 524/381 |
| 4,716,203 | 12/1987 | Casey et al. | 525/408 |
| 4,739,773 | 4/1988 | Schmitt et al. | 128/92 R |
| 4,744,365 | 5/1988 | Kaplan et al. | 528/354 |
| 4,745,160 | 5/1988 | Churchill et al. | 525/415 |
| 4,788,979 | 12/1988 | Jarrett et al. | 528/354 |
| 4,791,929 | 12/1988 | Jarrett et al. | 528/354 |
| 4,838,267 | 6/1989 | Jamiolkowski et al. | 325/415 |
| 4,857,602 | 8/1989 | Casey et al. | 525/408 |
| 4,891,263 | 1/1990 | Kothar et al. | 528/370 |
| 4,896,802 | 1/1990 | Williams | 128/149 |
| 4,916,193 | 4/1990 | Tang et al. | 525/413 |
| 4,916,207 | 4/1990 | Boyles, Jr. et al. | 528/370 |
| 4,920,203 | 4/1990 | Tang et al. | 525/409 |
| 5,007,923 | 4/1991 | Bezwada et al. | 525/411 |
| 5,019,094 | 5/1991 | Bezwada et al. | 606/230 |
| 5,037,950 | 8/1991 | Bezwada et al. | 528/334 |
| 5,066,772 | 11/1991 | Tang et al. | 528/354 |
| 5,080,665 | 1/1992 | Jarrett et al. | 528/354 |
| 5,120,802 | 6/1992 | Mares et al. | 525/415 |
| 5,133,739 | 7/1992 | Bezwada et al. | 528/357 |
| 5,145,945 | 9/1992 | Tang et al. | 528/370 |
| 5,152,781 | 10/1992 | Tang et al. | 606/230 |
| 5,185,408 | 2/1993 | Tang et al. | 525/415 |
| 5,225,520 | 7/1993 | Kennedy et al. | 528/354 |
| 5,236,444 | 8/1993 | Muth et al. | 525/411 |
| 5,252,701 | 10/1993 | Jarrett et al. | 528/354 |
| 5,314,989 | 5/1994 | Kennedy et al. | 525/415 |
| 5,322,925 | 6/1994 | Muth et al. | 525/415 |

FOREIGN PATENT DOCUMENTS

| 779291 | 7/1957 | United Kingdom . |
| 1332505 | 10/1973 | United Kingdom . |
| 1414600 | 11/1975 | United Kingdom . |
| 2102827 | 2/1983 | United Kingdom . |

OTHER PUBLICATIONS

D. K. Gilding, et al., "Biodegradable Polymers for use in surgery–polyglycolic/polyhomo–and copolymers: 1" Polymer, vol. 20, pp. 1459–1464 (79).

D. F. Williams (ed.) Biocompatibility of Clinical Implant Materials, vol. II, Chapter 9: "Biodegradable Polymers" (1981).

*Primary Examiner*—David Buttner

[57] ABSTRACT

Block copolymers have one of the block made from hard phase forming monomers and another block made from soft phase forming monomers copolymerized with randomly intermingled units of other soft phase forming monomers. Particularly useful copolymers are initiated with a polyalkylene oxide initiator. The copolymers are useful in forming surgical articles, including both monofilament and multifilament sutures.

19 Claims, 1 Drawing Sheet

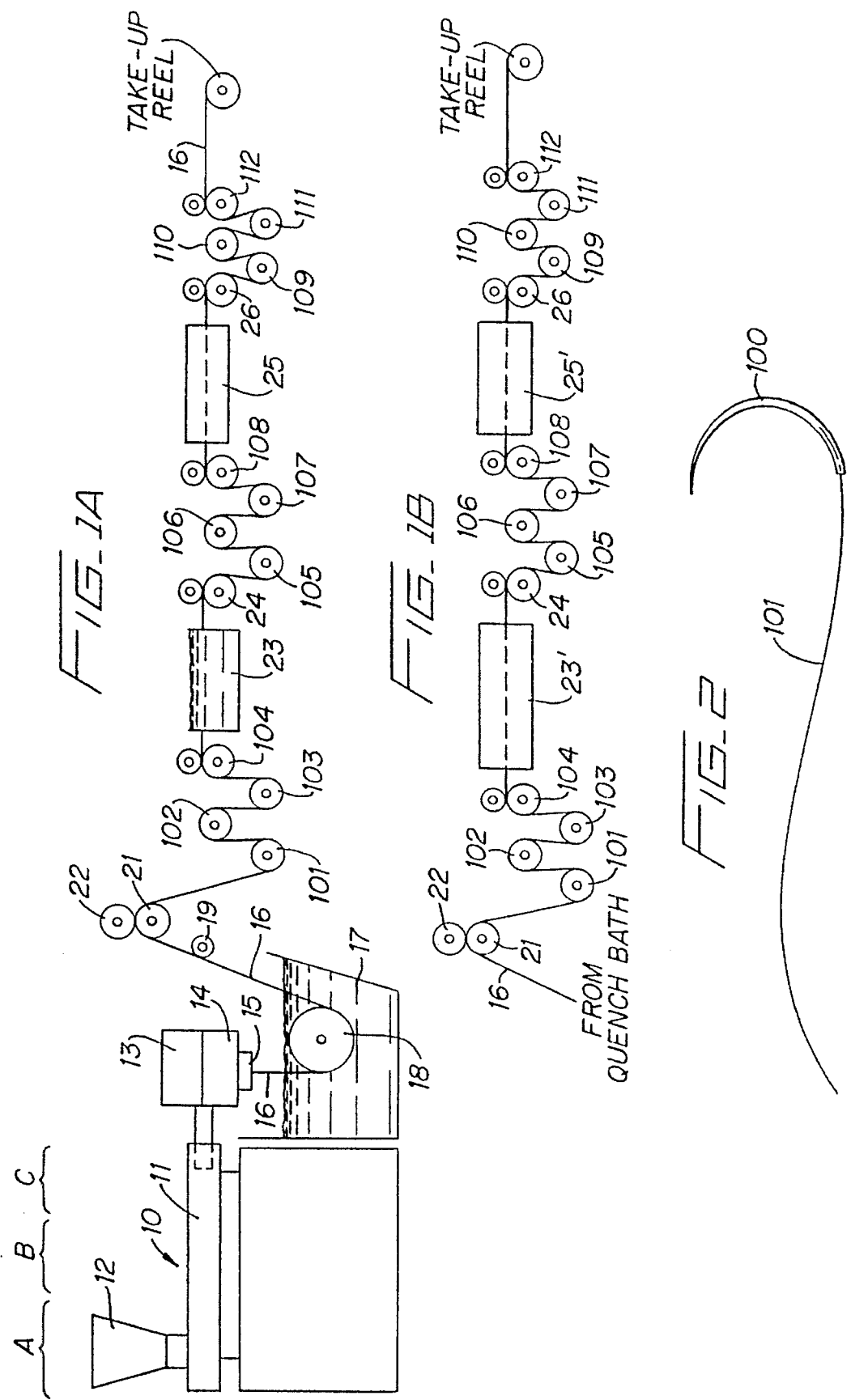

ABSORBABLE BLOCK COPOLYMERS AND SURGICAL ARTICLES FABRICATED THEREFROM

This application is a continuation-in-part of pending U.S. patent application Ser. No. 08/204,721 filed Mar. 2, 1994 U.S. Pat. No. 5,403,347 which is a continuation-in-part of U.S. patent application Ser. No. 08/068,811 filed May 27, 1993 now abandoned.

TECHNICAL FIELD

The present disclosure relates to absorbable block copolymers. More specifically, absorbable block copolymers initiated with polyalkylene oxide, and have one block made predominantly of hard phase forming monomers and another block made from randomly copolymerized soft phase forming monomers are provided. Surgical articles including both monofilament and multifilament sutures, can be made totally or in part from the absorbable block copolymers.

BACKGROUND OF RELATED ART

Polymers and copolymers of, and surgical devices made from lactide and/or glycolide and/or related compounds are well-known. See, e.g., U.S. Pat. Nos. 2,668,162, 2,683,136, 2,703,316, 2,758,987, 3,225,766:, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for use in surgery-polyglycolic/poly (lactic acid) homo-and copolymers: 1, "*Polymer*, Volume 20, pages 1459–1464 (1979), and D. F. Williams (ed.) *Biocompatibility of Clinical Implant Materials*, Volume II, chapter 9: "Biodegradable Polymers" (1981). Surgical devices prepared from copolymers containing lactide or glycolide and trimethylene carbonate have been described.

U.S. Pat. No. 4,429,080 describes glycolide end blocks and glycolide trimethylene carbonate random copolymer middle blocks. The block copolymers described in the '080 patent contain no 1,4 dioxane-2-one.

As another example, U.S. Pat. No. 5,066,772 describes random copolymers of lactide and trimethylene carbonate and triblock copolymers having lactide end blocks and lactidetrimethylene carbonate random copolymer center blocks. The block copolymers of the '772 patent do not include a block which has predominantly glycolic acid ester linkages.

Block copolymers described in U.S. Pat. 5,145,945 do not include a block having random copolymers of trimethylene carbonate and dioxanone nor do they include a block which is predominantly glycolide. In addition, see U.S. Pat. Nos. 4,243,775; 4,300,565; 4,705,820; 4,891,263; 4,916,193; 4,902,203; 5,037,950, and 5,252,701.

U.S. Pat. No. 4,452,973 describes triblock copolymers having polyglycolic acid end blocks and polyalkylene oxide middle blocks. Polyalkylene oxide also serves as a polymerization initiator for the polyglycolic acid blocks. U.S. Pat. No. 5,076,807 describes the use of polyalkylene glycol initiators for producing copolymers of dioxanone, glycolide and lactide.

Triblock copolymers having polyalkylene oxide middle blocks, are described in U.S. Pat. Nos. 4,438,253, 4,526,938, 4,716,203, 4,745,160, 4,857,602, and 5,019,094.

As described above synthetic bioabsorbable sutures are known in the art. However, in the manufacture of sutures an important characteristic of a suture is the amount of effort typically required to straighten the suture upon its removal from the package in order to ready the suture for use. This effort appears to be related to the "strain energy" of the suture, i.e., the integration of the stress-strain curve for the suture measured in kilogram-mm, and is equivalent to the work expended in elongating the monofilament by a specified percentage of its original length. As the strain energy of a given size of suture decreases so, too, does the amount of effort required to straighten the suture prior to use. A decrease in strain energy also appears to relate to the perceived flexibility of the suture, another important characteristic.

Another desirable characteristic of a bioabsorbable suture is its ability to exhibit and maintain desired tensile properties for a predetermined time period.

Absorbable sutures are manufactured from natural or synthetic materials. Synthetic absorbable multifilament sutures such as Dexon, Vicryl, and Polysorb commercially available from Davis & Geck (Danbury, Conn.), Ethicon, Inc. (Sommerville, N.J.), and United States Surgical Corporation (Norwalk, Conn.), respectively, are known in the industry as short term absorbable sutures. The classification short term absorbable sutures generally refers to surgical sutures which retain about 20 percent of their original strength at three weeks after implantation.

Long term absorbable sutures are generally known to be sutures which retain about 20 percent of their original strength at six or more weeks after implantation. For example PDS II and Maxon, synthetic absorbable monofilament sutures, commercially available from Ethicon, Inc. (Sommerville, N.J.) and Davis & Geck (Danbury, Conn.), generally fit this absorption profile.

Some of the earliest absorbable sutures were made from non-synthetic collagenous material taken from sheep's intestines. Such non-synthetic bioabsorbable sutures are still in use today and are commonly referred to as "catgut" or "gut sutures". Such sutures generally absorb quicker than short term absorbable sutures; retaining about 20 percent of their original strength at only two weeks after implantation. However, gut sutures may be undesirably stiff before subsequent treatment which renders them flexible and pliable. Commercially available gut sutures are immersed in tubing fluids (liquids used to achieve or enhance flexibility and pliability as well as to preserve the gut sutures, without effecting the suture's strength or integrity.), sterilized, and supplied to surgeons in packages containing the tubing solution.

Therefore, it would be advantageous to provide a bioabsorbable synthetic monofilament surgical suture which exhibits and maintains tensile properties and handling characteristics comparable to gut sutures, while providing the desired tensile strength retention profile and eliminating the need for tubing fluids.

SUMMARY

It has now been found that absorbable surgical articles may be formed from a block copolymer having one of the blocks made from hard phase forming monomers and another of the blocks made from random copolymers of soft phase forming monomers. Hard phase forming monomers include glycolide and lactide while soft phase forming monomers include 1,4 dioxane-2-one and 1,3 dioxane-2-one and caprolactone.

Preferably, block copolymers useful in forming surgical articles disclosed herein include block copolymers comprising one block having glycolic acid ester units as a predominant component thereof. A "predominant component" is a component which is present in an amount greater than 50 percent.

In a particularly useful embodiment the block copolymers may be spun into fibers. The fibers can be fabricated into both monofilament and braided multifilament sutures.

In another aspect, the absorbable block copolymers can be formed using a polyalkylene oxide initiator. Copolymers in accordance with this embodiment generally retain about 20 percent of their original strength at two weeks after implantation which approximates that of gut sutures. Such sutures do not require immersion in a tubing solution to exhibit suitable tensile properties or flexibiltity and pliablility.

In yet another aspect, a process is provided for manufacturing a suture exhibiting excellent energy and/or increased knot performance for a given size comprising the operations of extruding the block copolymer of the present invention at an extrusions temperature of from about 170° C. to about 250° C. to provide a monofilament fiber, stretching the solidified monofilament at a temperature of from about 20° C. to about 90° C. in water (or other suitable liquid medium) or at from about 30° C. to about 100° C. in air (or other suitable gaseous medium) at a stretch ratio of from about 3:1 to about 10:1 to provide a stretched monofilament. The stretched monofilament preferably is then frozen at a temperature of from about −15° C. to about 0° C. The suture then may be annealed with or without relaxation at a temperature of from about 80° C. to about 130° C. to provide the finished suture.

BRIEF DESCRIPTION OF THE DRAWINGS

FIG. 1A is a schematic illustration of an apparatus which is suitable for manufacturing monofilament suture.

FIG. 1B is a modification of the apparatus of FIG. 1A which is particularly suitable for manufacturing the monofilament sutures of smaller size, e.g., sizes 4/0 and smaller.

FIG. 2 is a perspective view of a suture attached to a needle.

DETAILED DESCRIPTION OF PREFERRED EMBODIMENTS

It has been found that a block copolymer having two specific types of blocks, an "A" block having a proportion of glycolic acid ester units as the predominant component thereof and a "B" block comprising 1,3 dioxane-2-one randomly copolymerized with 1,4 dioxane-2-one, can advantageously be combined to form a block copolymer useful in forming surgical elements.

Block copolymer compositions include an A block formed from a copolymer which has glycolide as the predominant component thereof. That is, glycolide comprises at least 50 mole percent of the first block. Preferably, glycolide comprises at least about 60 mole percent of the first block and most preferably at least about 95 mole percent glycolide.

The glycolide may be copolymerized with any monomer which provides an absorbable copolymer to form the A block. Such monomers include but are not limited to lactide, trimethylene carbonate, p-dioxanone, and epsilon-caprolactone. The copolymers of glycolide which form the first block can be random or block copolymers and can be synthesized by known methods. See, for example. U.S. Pat. Nos. 4,653, 497; 4,838,267; 4,429,080; 4,605,730; and 4,788,979 the disclosures of which are incorporated herein by reference.

The B block of the block copolymer compositions has 1,4 dioxane-2-one and 1,3 dioxane-2-one linkages. Preferably 1,4 dioxane-2-one comprises from about 20 mole percent to about 80 mole percent, and more preferably from about 35 mole percent to about 65 mole percent of the B block. Most preferably, 1,4 dioxane-2-one comprises at least about 35 mole percent of the B block, the remainder of the block comprising 1,3 dioxane-2-one. Copolymers of 1,3 dioxane-2-one and 1,4 dioxane-2-one having an inherent viscosity of from about 0.5 to about 2 dl/g measured at 30° C. and a concentration of 0.25 g/dl in chloroform or HFIP may generally be used as the second block.

The block copolymers may be prepared by preparing the individual polymers which make up the blocks and then copolymerizing these polymers to form a block or graft copolymer. Alternatively, a pre-polymer having 1,4 dioxane-2-one and 1,3 dioxane-2-one linkages may be prepared in a reactor and then the monomers needed to form the other block or blocks are added directly to the reactor to thereby form the block copolymer. In one embodiment the polymerization reaction used in the formation of the above mentioned pre-polymer is stopped short of completion, leaving residual 1,4 dioxane-2-one. Then monomers needed to form the other block or blocks are added directly to the reactor vessel to react with the residual 1,4 dioxane-2-one and the pre-polymer to form block copolymers having 1,4 dioxane-2-one linkages in each block.

In forming the block copolymers, the A (predominantly glycolide) block may be present in an amount from about 50 to about 80 percent by weight based on the weight of the final block copolymer. The B (random copolymer) block may be present in an amount from about 20 to about 50 weight percent based on the weight of the final block copolymer. Preferably, the A block comprises between about 60 and about 70 weight percent of the block copolymer. In a particularly useful embodiment, the A block comprises about 70 weight percent and the B block comprises about 30 weight percent of the final block copolymer. The copolymers preferably have a molecular weight such that their inherent viscosity is from about 0.8 to about 1.6 dl/g, and more preferably from about 1 to about 1.40 dl/g measured at 30° C. at a concentration of 0.25 g/dl in chloroform or hexafluoroisopropanol (HFIP).

Each A and B block may comprise a single type of recurring monomeric unit. Alternatively, each block may comprise more than one type of recurring monomeric unit randomly distributed throughout each block. The block copolymers of the present invention may have repeating block units such as AB, ABA, ABAB, ABABA, BABA, ABBA; with ABA or ABBA being preferred.

Monofunctional, difunctional and polyfunctional initiators can be used to prepare the copolymers. In this particular embodiment preferred initiators are monofunctional, difunctional and polyfunctional polyalkylene oxides. Polyalkylene oxides such as, for example, diethylene glycol, polyethylene oxide, polyethylene glycol diol, polyethylene glycol methyl ether, and polypropylene glycol are particularly useful initiators. Suitable polyalkylene oxide initiators also include polypropylene oxide-polyethylene oxide copolymers sold under the trademark "PLURONIC" by BASF Corporation. Polyethylene oxide, commonly known as polyethylene glycol, is the most preferred initiator for preparing the copolymers described herein. Polymerization in the presence of polyalkylene oxides provides copolymers for use in preparing surgical articles that exhibit good flexibility and handling characteristics as well as desirable in vivo tensile strength retention of about 14 days or less.

Where a polyalkylene oxide is used as an initiator to prepare the present copolymers, the copolymers will include a center block of polyalkylene oxide. In this embodiment, the center block preferably constitutes about 0.1 to about 5 percent by weight of the block copolymer and more preferably from about 0.2 to about 3.5 percent by weight of the block copolymer, the A block is preferably from about 50 to about 80 percent by weight of the copolymer and the B block is preferably from about 20 to about 50 percent by weight of the copolymer.

The present block copolymers can be formed into surgical articles using any known technique, such as, for example, extrusion, molding and/or solvent casting. The copolymers can be used alone, blended with other absorbable compositions, or in combination with non-absorbable components. A wide variety of surgical articles can be manufactured from the novel copolymers disclosed herein. These include but are not limited to clips and other fasteners, staples, sutures, pins, screws, prosthetic devices, wound dressings, drug delivery devices, anastomosis rings, and other implantable devices. Fibers made from the copolymers of this disclosure can be knitted or woven with other fibers, either absorbable or nonabsorbable to form meshes or fabrics. The present compositions can also be used as an absorbable coating for surgical devices. Preferably, however, the copolymers are spun into fibers to be used as sutures, either monofilament or multifilament.

Multifilament sutures in accordance with this disclosure may be made by methods known in the art. Braid constructions such as those disclosed and claimed in U.S. Pat. Nos 5,059,213 and 5,019,093 are suitable for the multifilament suture of the present copolymers.

A suitable process for the manufacture of monofilament sutures comprises the operations of melt extruding the resin at an extrusion temperature of from about 170° C. to about 250° C. to provide a monofilament, stretching the solidified monofilament at a temperature of from about 20° C. to about 90° C. in water (or other suitable liquid medium) or at from about 30° C. to about 100° C. in air (or other suitable gaseous medium) at a stretch ratio of from about 3:1 to about 10:1 to provide a stretched monofilament. Optionally, the solidified monofilament may be stretched in air or other suitable gaseous medium preferably at about 30° C. to about 105° C. Preferably, the monofilament is then frozen at a temperature of from about −15° C. to about 0° C. The suture may then be annealed at a temperature of from about 50° C. to about 130° C. to provide the finished suture.

FIG. 1A schematically illustrates a monofilament suture manufacturing operation which is especially suitable for producing larger size sutures, e.g., those of sizes 2/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the block copolymers of the present invention which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 170° C. to 220° C., zone B at from about 180° C. to 230° C. and zone C at from about 190° C. to about 240° C. Additional temperature parameters include: metering pump block 13 at from about 180° C. to about 230° C., spin pack 14 at from about 190° C. to about 230° C., spinneret 15 at from about 180° C. to about 230° C. and quench bath at from about 10° C. to about 80° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation; and subsequently wrapped around godets 101, 102, 103 and 104 or any other suitable godet arrangement. Monofilament 16 passing from godet 104 is stretched, e.g., with stretch ratios on the order of from about 3:1 to about 10:1 and preferably from about 4:1 to about 7:1, to effect its orientation and thereby increase its tensile strength.

In the stretching operation shown in FIG. 1A, generally suitable for larger size sutures, e.g., sizes 2 to 2/0, monofilament 16 is drawn through hot water (or other suitable liquid medium) draw bath 23 by means of godets 24, 105, 106, 107 and 108 or any other suitable arrangement of godets which rotate at a higher speed than godet 104 to provide the desired stretch ratio. The temperature of hot water draw bath 23 is advantageously from about 30° C. to about 90° C. and preferably is from about 30° C. to about 50° C.

In the alternative stretching operation shown in FIG. 1B, generally preferred for smaller sutures sizes, e.g., sizes 3/0 to 8/0, monofilament 16 is drawn by godets 24, 105, 106, 107, and 108 or any other suitable godet arrangement through hot air convection oven chamber 23' at a temperature of from about 30° C. to about 80° C. and preferably from about 30° C. to about 60° C. to provide the desired amount of stretch. Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 26, 109, 110, 111, and 112 or any other suitable godet arrangement through second hot air oven chamber 25 at a temperature of from about 30° C. to about 120° C. and preferably from about 30° C. to about 60° C. During the relaxation process, at these temperatures, monofilament 16 will generally recover to within about 80 to about 97 percent, and preferably to within about 95 percent, of its pre-annealed length to provide the finished suture. For relaxation, the third godet rotates at a slower speed than the second godet thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 70° C. to about 150° C., as described in U.S. Pat. No. 3,630,205. After a suitable period of residency in the heating cabinet, e.g., about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

The suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this disclosure to incorporate one or more medico-surgically useful substances into articles prepared according to the present disclosure, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures of the present disclosure in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, the sutures are dyed by adding up to about a few percent and preferably about 0.2% dye, such as D&C Violet No. 2 to the resin prior to extrusion.

In order that those skilled in the art may be better able to practice the present invention, the following examples are given as an illustration of the preparation of the novel block copolymers described herein as well as of the preparation and superior characteristics of the sutures made from the present novel copolymers. It should be noted that the invention is not limited to the specific details embodied in the examples and further that all ratios or parts recited are by weight.

EXAMPLE 1

1,3 dioxane-2-one (1137.5 grams) and 1,4 dioxane-2-one (741 grams) are added to a reactor along with 0.5 grams of stannous chloride and 1 gram of diethylene glycol. The mixture is heated and placed at 150° C., with stirring under a nitrogen atmosphere for 3.5 hours. The setting of the reactor is then decreased to 130° C. and stirring is continued for 3 hours. The 1,3 dioxane-2-one /1,4 dioxane-2-one copolymer is then sampled.

Five hundred grams of dry glycolide are then added to the reactor. The setting for the temperature of the reactor is then increased to 210° C. When the temperature of the reactor reaches 195° C., 2750 grams of glycolide are added with continued stirring. The polymerization is continued for about 45 minutes. The reaction product is isolated, comminuted, and treated to remove residual reactants using known techniques.

EXAMPLE 2

1,3 dioxane-2-one (1300 grams) and 1,4 dioxane-2-one (840 grams) are added to a reactor along with 0.5 grams of stannous chloride and 1 gram of diethylene glycol. The mixture is heated and placed at 150° C. (with stirring) under a nitrogen atmosphere for 3.5 hours. The setting of the reactor is then decreased to 130° C. and stirring is continued for 3 hours. The 1,3 dioxane-2-one/1,4 dioxane-2-one copolymer is then sampled.

Five hundred grams of dry glycolide are then added to the reactor. The setting for the temperature of the reactor is then increased to 210° C. when the temperature of the reactor reaches 195° C., 2500 grams of glycolide are added with continued stirring. The polymerization is continued for about forty five minutes.

The reaction product is isolated comminuted, and treated to remove residual reactants using known techniques. The copolymer is then heated under vacuum to remove residual water, residual solvent and/or unreacted monomer.

EXAMPLE 3

1,3 dioxane-2-one (1300 g) and 1,4 dioxane-2-one (840 grams) are added to a reactor along with 0.5 grams of stannous chloride and 10 grams of polyethylene oxide (m.w. 1000). The mixture is heated at 150° C., with stirring under a nitrogen atmosphere for 3.5 hours. The temperature setting of the reactor is then decreased to 130° C. and stirring is continued for 3 hours. The 1,3 dioxane-2-one/1,4 dioxane-2-one copolymer is then sampled, and five hundred grams of dry glycolide are added to the reactor. The setting for the temperature of the reactor is increased to 210° C. When the temperature of the reactor reaches 195° C., 2500 grams of glycolide are added with continued stirring. The polymerization is continued for about 45 minutes.

The reaction product is isolated, comminuted, and treated to remove residual reactants using known techniques. The copolymer is then heated under vacuum to remove residual water, residual solvent and/or unreacted monomer.

EXAMPLE 4

1,3 dioxane-2-one (1300 g) and 1,4 dioxane-2-one (840 grams) are added to a reactor along with 0.5 grams of stannous chloride and 160 grams of polyethylene glycol (P.E.G. diol) having 8,000 molecular weight. The mixture is heated at 150° C., with stirring under a nitrogen atmosphere for 3.5 hours. The temperature setting of the reactor is then decreased to 130° C. and stirring is continued for 3 hours. The 1,3 dioxane-2-one/1,4 dioxane-2-one copolymer is then sampled, and five hundred grams of dry glycolide are added to the reactor. The setting for the temperature of the reactor is increased to 210° C. When the temperature of the reactor reaches 195° C., 2500 grams of glycolide are added with continued stirring. The polymerization is continued for about 45 minutes.

The reaction product is isolated, comminuted, and treated to remove residual reactants using known techniques. The copolymer is then heated under vacuum to remove residual water, residual solvent and/or unreacted monomer.

Table I below sets forth typical conditions for extruding, stretching various sizes of sutures in accordance with this disclosure. All of the monofilament sutures were fabricated from the resin of Example 1, Example 2, Example 3 and Example 4.

TABLE I

CONDITIONS OF MANUFACTURING MONOFILAMENT SUTURES OF THE PRESENT INVENTION

| Example | 1 | 2 | 3 | 4 |
|---|---|---|---|---|
| Suture Size | 3/0 | 3/0 | 3/0 | 3/0 |
| Process Conditions | | Extrusion Operation | | |
| extruder screw, rpm | 3.1 | 1.6 | 1.4 | 2.0 |
| pump, rpm | 12.6 | 6.1 | 9.2 | 7.1 |
| barrel temp., °C., zone A | 195 | 190 | 193 | 185 |
| barrel temp., °C., zone B | 200 | 196 | 197 | 205 |
| barrel temp., °C., zone C | 208 | 200 | 206 | 205 |
| clamp temp., °C., | 208 | 200 | 205 | 205 |
| adapter temp., °C. | 208 | 200 | 202 | 205 |
| pump temp., °C. | 209 | 195 | 201 | 205 |
| block temp., °C. | 209 | 195 | 207 | 215 |
| barrel melt temp., °C. | 201 | 208 | 200 | 175 |
| pump melt temp., °C. | 202 | 198 | 206 | 170 |
| spinneret melt temp., °C. | 202 | 201 | 214 | 195 |
| barrel pressure, psi | 1400 | 1758 | 1350 | 640 |
| pump pressure, psi | 1400 | 1791 | 500 | 350 |
| spinneret pressure, psi | 900 | 882 | 2110 | 720 |
| pump size, cc per revolution | 0.16 | 0.297 | 0.297 | 0.297 |
| diameter of spinneret, orifices, mm | 1.25 | 1.25 | 1.25 | 1.25 |
| no. of spinneret orifices | 1 | 1 | 1 | 1 |
| quench bath temp., °C. | 17 | 20 | 22 | 21 |
| | Stretching (Orienting) Operation | | | |
| draw bath temp., °C. | 32 | 32 | — | — |
| First oven temp, °C. | — | — | 30 | 30 |
| first godet, mpm | 4.6 | 5.3 | 5.2 | 4.5 |
| second godet, mpm | 30 | 29.4 | 24.0 | 22.5 |
| second oven temp., °C. | 33 | 33 | 105 | — |
| third godet, mpm | 30 | 29.3 | 32.8 | 31.5 |
| draw ratio | 6.5:1 | 5.5:1 | 6.3:1 | 7.0:1 |

TABLE I-continued

CONDITIONS OF MANUFACTURING MONOFILAMENT SUTURES OF THE PRESENT INVENTION

| Example | 1 | 2 | 3 | 4 |
|---|---|---|---|---|
| | Freezing Operation | | | |
| temp., °C. | −13 | −13 | −13 | −13 |
| time (hrs.) | 18 | 18 | 18 | 18 |
| | Annealing Operation | | | |
| oven temp., °C. | 105 | 70 | 105 | 105 |
| time (hrs.) | 18 | 18 | 6 | 6 |

The physical properties of the sutures and the procedures employed for their measurement are set forth in Table II as follows:

TABLE II

PROCEDURES FOR MEASURING PHYSICAL PROPERTIES OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm$^2$ | ASTM D-2256, Instron Corporation Series IX Automated Materials Testing System 1.03A |
| 0–5% and 0–10% strain energies, kg-mm | ASTM D-2256, Instron Corporation Series IX Automated Materials Testing System 1.03A |

Table III below sets forth the physical properties of the size 3/0 sutures of Examples 1–4.

TABLE III

| Physical Property | Example 1 | Example 2 | Example 3 | Example 4 |
|---|---|---|---|---|
| diameter (mm) | 0.3 | 0.29 | 0.317 | 0.294 |
| knot-pull strength (kg) | 2.9 | 2.4 | 3.2 | 2.6 |
| Young's Modulus (kpsi) | 190 | 145 | 220 | 161 |
| Straight-pull strength (kg) | 4.4 | 3.7 | 6.9 | 4.6 |
| Strain Energy 0–5% (kg-mm) | 1.28 | 0.84 | 1.19 | 1.06 |
| Strain Energy 0–10% (kg-mm) | 3.89 | 2.76 | 3.72 | 3.22 |
| Elongation (%) | 47 | 44 | 40 | 38 |
| Tensile Strength (kg/mm$^2$) | 60.6 | 55.3 | 88.2 | 67.2 |

COMPARATIVE EXAMPLE

TABLE IV Below sets forth the physical properties of a size 3/0 Maxon suture, which is made from a glycolide/glycolide-co-trimetlylene carbonate/glycolide copolymer (commercially available from Davis & Geck, Danbury, Conn.)

TABLE IV

| | |
|---|---|
| diameter (mm) | 0.293 |
| Knot-pull strength (kg) | 2.9 |
| Young's Modulus (kpsi) | 425 |

TABLE IV-continued

| | |
|---|---|
| Straight-pull strength (kg) | 3.9 |
| Strain Energy 0–5% (kg-mm) | 1.6 |
| Strain Energy 0–10% (kg-mm) | 5.19 |
| Elongation (%) | 30 |
| Tensile Strength (kg/mm$^2$) | 56.2 |

As the data in Tables III and IV illustrate, the sutures made of the present novel copolymers showed improved flexibility while demonstrating acceptable physical properties, such as knot pull and straight-pull strength as compared to commercially available synthetic absorbable monofilament sutures of the same size.

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A block copolymer comprising:
   a) a polyalkylene oxide block;
   b) at least one block containing a proportion of glycolic acid ester units; and
   c) at least one other block comprising 1,4 dioxan-2-one randomly polymerized with 1,3 dioxane-2-one.

2. The block copolymer of claim 1, wherein glycolic acid ester units comprise from about 50 to about 80 percent by weight of said block copolymer.

3. The block copolymer of claim 1, wherein said blocks comprising random copolymers of 1,4 dioxan-2-one and 1,3 dioxane-2-one comprise from about 20 to about 50 percent by weight of said block copolymer.

4. The block copolymer of claim 3, wherein said blocks comprising random copolymers of 1,4 dioxan-2-one and 1,3 dioxane-2-one are formed from the random polymerization of about 35 percent by weight of 1,4 dioxan-2-one and about 65 percent by weight 1,3 dioxane-2-one.

5. The block copolymer of claim 1, wherein component (b) comprises a predominant amount of glycolic acid ester units, the remainder being 1,4 dioxane-2-one.

6. The block copolymer of claim 5 wherein component (c) consists essentially of 1,4 dioxane-2-one randomly polymerized with 1,3 dioxane-2-one.

7. The block copolymer according to claim 1, wherein said polyalkylene oxide block is formed from an initiator selected from the group consisting of polyethylene oxide, polypropylene oxide, diethylene glycol, polyethylene glycol, polyethylene glycol diol, polyethylene glycol methyl ether, polypropylene glycol and copolymers of ethylene oxide and propylene oxide.

8. The block copolymer of claim 1, wherein said block copolymer is a penta-block copolymer.

9. The block copolymer of claim 8, wherein said polyalkylene oxide block is the center block; at least one of said blocks comprising 1,4 dioxan-2-one randomly polymerized with 1,3 dioxane-2-one is adjacent said center block; and at least one of said blocks containing a proportion of glycolic acid ester units is adjacent said blocks comprising 1,4 dioxan-2-one randomly polymerized with 1,3 dioxane-2-one.

10. A surgical article formed totally or in part from the block copolymer of claim 1.

11. The surgical article of claim 10, wherein said surgical article is selected from the group consisting of clips, staples, sutures, pins, screws, prosthetic devices, anastomosis rings, and growth matrices.

12. The surgical article of claim 10, wherein said surgical article is a suture which retains its in vivo tensile strength for about 14 days.

13. A method of making a copolymer comprising the steps of:
   a) adding 1,4 dioxane-2-one and 1,3 dioxane-2-one to a reactor;
   b) polymerizing component (a) in the presence of a polyalkylene oxide initiator to the point where all the 1,3 dioxane-2-one is incorporated in a polymer but residual 1,4 dioxane-2-one monomer remains;
   c) adding glycolide; and
   d) polymerizing.

14. The method according to claim 13, wherein said polyalkylene oxide initiator is selected from the group consisting of polyethylene oxide, polypropylene oxide, diethylene glycol, polyethylene glycol, polyethylene glycol diol, polyethylene glycol methyl ether, polypropylene glycol and copolymers of ethylene oxide and propylene oxide.

15. A copolymer obtained in accordance with the method of claim 13.

16. A suture fabricated from a copolymer, said copolymer comprising:
   a) a polyalkylene oxide center block;
   b) at least one block containing a proportion of glycolic acid ester units; and
   c) at least one other block comprising 1,4 dioxan-2-one randomly polymerized with 1,3 dioxane-2-one.

17. The suture of claim 16 exhibiting in vivo tensile strength retention for about 14 days.

18. The suture of claim 16 which is a monofilament suture.

19. A method of suturing a wound comprising:
   a) providing a needled suture, the suture being fabricated from a block copolymer comprising:
      i) a center block of polyalkylene oxide,
      ii) at least one block containing a proportion of glycolic acid ester units, and
      iii) at least one other block comprising 1,4 dioxan-2-one randomly polymerized with 1,3 dioxane-2-one; and
   b) passing said needled suture through tissue to create wound closure.

* * * * *